United States Patent [19]

Okonogi et al.

[11] 4,172,126
[45] Oct. 23, 1979

[54] METHOD FOR THE INACTIVATION OF MICROBIAL TOXINS AND ATTENUATION OF VACCINES

[75] Inventors: Takashi Okonogi; Zenpachiro Hattori; Akira Ogiso; Seiji Mitsui, all of Tokyo, Japan

[73] Assignee: Sankyo Company Limited, Tokyo, Japan

[21] Appl. No.: 846,149

[22] Filed: Oct. 27, 1977

[30] Foreign Application Priority Data

Nov. 8, 1976 [JP] Japan ................................. 51/133956
Mar. 8, 1977 [JP] Japan ................................. 52/25309

[51] Int. Cl.² ..................... A61K 39/02; A61K 39/08; A61K 39/12

[52] U.S. Cl. .......................................... 424/92; 424/88; 424/89; 435/245; 435/885; 435/822; 435/842; 435/844

[58] Field of Search ..................... 195/1.4; 424/88, 89, 424/92

[56] References Cited

PUBLICATIONS

Majsky–Chem. Abst., vol. 52 (1958), p. 17502g.
Beladi et al.–Chem. Abst., vol. 64 (1966), p. 20226c.

*Primary Examiner*—Sam Rosen
*Attorney, Agent, or Firm*—Toren, McGeady and Stanger

[57] ABSTRACT

A method for the inactivation of microbial toxins and attenuation of vaccines by treating the toxin or vaccine with a tannin, especially a condensed tannin derived from fruit of the genus Diospyros, particularly the persimmon, without loss of the desired antigenicity.

14 Claims, 4 Drawing Figures

ELUTED AMOUNT

METHOD FOR THE INACTIVATION OF MICROBIAL TOXINS AND ATTENUATION OF VACCINES

This invention relates to the inactivation of microbial toxins and the attenuation of vaccines and to a new condensed tannin having this utility.

BACKGROUND OF THE INVENTION

Toxins produced by microbial agents, for example bacteria, can be used as antigens in the process of active immunisation, where the production of antibodies is stimulated by the introduction of a specific antigen. Frequently, the toxin must be inactivated so that it can be administered safely, while at the same time its antigenic effect must be maintained. An inactivated toxin, known as toxoid, is commonly prepared from various microorganisms by the addition of formaldehyde. Another compound used for this purpose is tannic acid, obtained from fermented oak galls.

The manufacture of toxoids and vaccines involves very close quality control and the products require special handling and storage. Legislation has been passed in many countries controlling the manufacture, storage and use of vaccines in order to ensure the maximum safety.

Nevertheless, biological preparations of this type exhibit various side-effects which are unavoidable even under strict control. For instance, pertussis vaccine, which is epidemiologically regarded as a necessity, especially in developing areas such as South East Asia and Africa, is known to produce side-effects such as swelling at the inoculation site, pain, systemic fever, vomitting and also symptoms of shock or, occasionally, serious brain damage. There is thus a real need for a method which will eradicate the unpleasant side-effects of such a vaccine, while at the same time the prophylactic effect is maintained.

SUMMARY OF THE INVENTION

We have now found that tannin derived from the persimmon and related species can be used to inactivate microbial toxins and to attenuate vaccines without affecting their antigenicity.

The fruit of the persimmon (*Diospyros Kaki* Thumb.) contains tannin, a simple aqueous extraction of which is known as an astringent and as a fining agent in the production of sake in Japan. The present invention is based on the surprising discovery that tannin from the persimmon fruit and the fruit of related species of Diospyros has a wholly unexpected effect on the toxins produced by microorganisms and on the side-effects of various vaccines.

According to the present invention there is provided a method for the inactivation of a microbial toxin or the attenuation of a vaccine, which comprises contacting the toxin or including in the vaccine tannin derived from fruit of the genus Diospyros.

The characteristics of the purified condensed tannin are illustrated in FIGS. 1 to 4 attached, in which FIG. 1 shows an ultra-violet absorption spectrum of the condensed tannin prepared in Example 1 measured in an aqueous solution having a concentration of 31.0 μg/ml;

DETAILED DESCRIPTION OF THE PREFERRED EMBODIMENT

The genus Diospyros is in the family Ebenaceae and includes, for example the persimmon itself (*Diospyros Kaki* Thumb.), the small persimmon (*Diospyros lotus* L.) and ebony (*Diospyros ebenum* Koenig).

The tannin may be extracted by any convenient method known and used in the extraction of vegetable tannins.

However, we have found that a particularly useful process for extracting the tannin comprises the steps of
(a) extracting the fruit with water or a water-miscible organic solvent or a mixture of water and a water-miscible organic solvent and removing insoluble matter;
(b) except where an alcoholic extraction solvent is used in step (a), concentrating the liquid extract, diluting with a lower alcohol and removing insoluble matter;
(c) precipitating tannin by adding to the alcoholic phase a non-solvent for tannin;
(d) dissolving the precipitated tannin in water, sterilising the solution and freeze-drying.

The extraction solvent in step (a) is preferably acetone, but alternatively another water-miscible solvent such as methanol or ethanol can be used. The non-solvent for the tannin, added to the alcoholic solution to precipitate the tannin, is conveniently an organic non-polar "solvent," such as an aliphatic ether, e.g., diethyl ether.

Preferably, the fruit, which may be ripe or unripe is first heated before being extracted in step (a). Heat treatment at, for example, 100° to 120° C. is advantageous. Step (a) is then effected, preferably on the minced fruit, either at ambient temperature or at an elevated temperature.

In step (d), the aqueous solution of the tannin is preferably dialysed before sterilisation, conveniently at an acid pH, e.g., pH 3–5, especially pH 4, obtained by addition of an acid such as hydrochloric acid, sulphuric acid or acetic acid.

The tannin is obtained as a pale brown powder.

We have found that when the extraction process detailed above is used, it is possible to obtain a condensed tannin free from other tannin materials, which is a new compound and forms part of the present invention.

Figure 1:
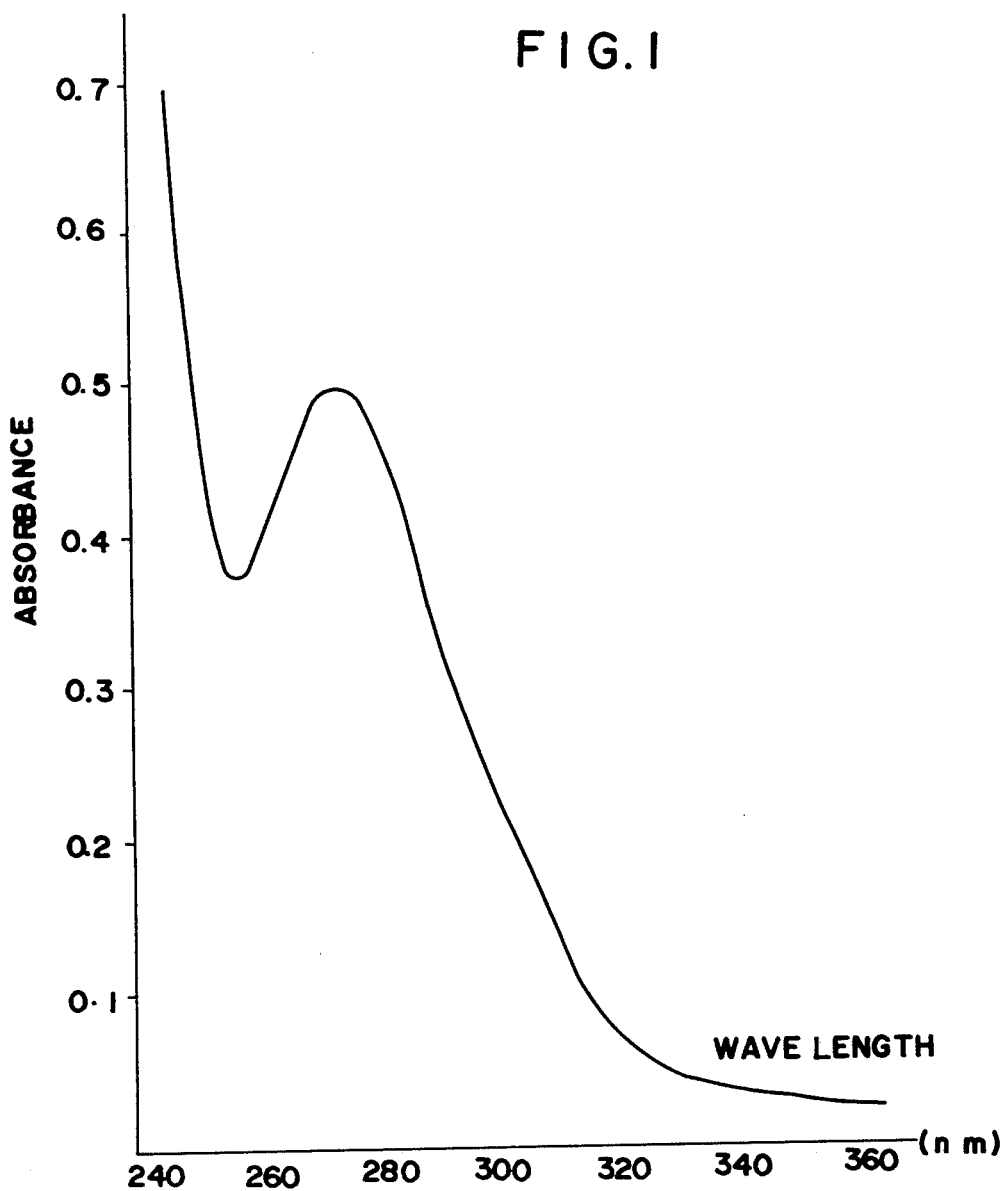
Figure 2:
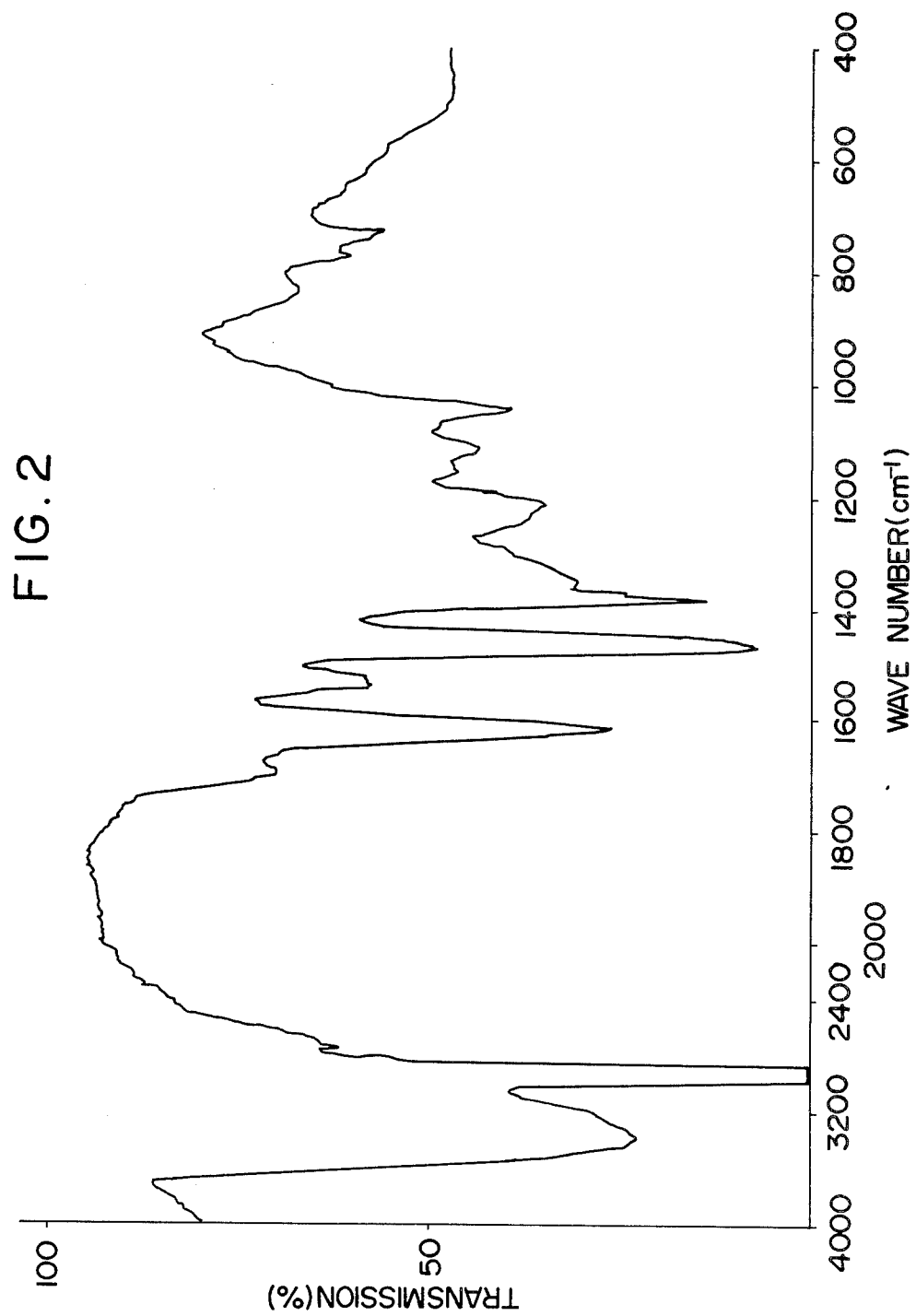
FIG. 2 shows an infra-red absorption spectrum of the same sample in liquid paraffin.
Figure 3:
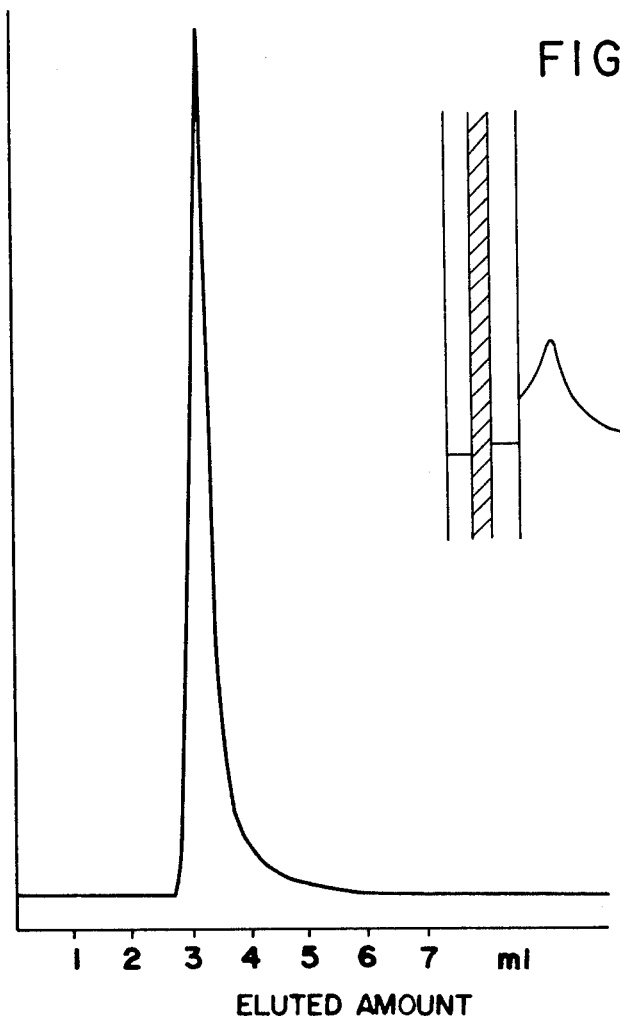
FIG. 3 shows a gel filtration chromatogram detected at an ultra-violet absorption of 254 nm wavelength at a temperature of 50° C. using a strongly acidic styrene-divinylbenzene copolymer sulphonate resin (Shodex HP-175) with water as the mobile phase.
Figure 4:
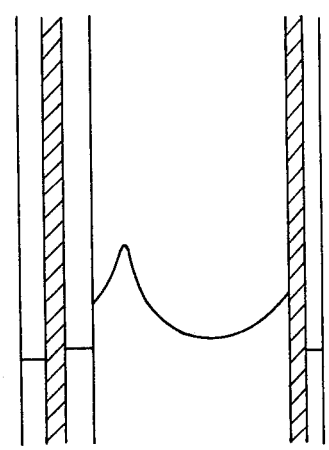
FIG. 4 shows an ultra-centrifuge Schlieren pattern of the same sample measured by dissolving the sample in 0.1 M phosphate buffer to a concentration of 1% and using an analytical ultra-centrifuge at 46,633 revs/min for 26 minutes.

Thus, according to the present invention there is further provided a condensed tannin derived from fruit of the genus Diospyros, having the following properties:
(a) a pale brown powder in the freeze-dried state;
(b) soluble in water; sparingly soluble in methanol, ethanol, pyridine, acetic acid; insoluble in diethyl ether, ethyl acetate, chloroform;
(c) aqueous solution gives a dark blue coloration with ferric chloride and a brown coloration with lead acetate;

(d) an infra-red absorption spectrum substantially as shown in FIG. 2 herein, when measured in liquid paraffin, having main adsorption bands at 3400, 1615, 1530, 1380, 1200, 1100 and 1040 cm$^{-1}$;

(e) an ultra-violet absorption spectrum substantially as shown in FIG. 1 herein when measured in an aqueous solution, having an absorption maximum at about 275 nm;

(f) a chromatogram substantially as shown in FIG. 3 herein having a single peak in a gel filtration using a strongly acidic styrene-divinylbenzene copolymer sulphonate resin column and water as a mobile phase; and (g) an ultra-centrifuge Schlieren pattern substantially as shown in FIG. 4 herein at about 46,633 revs/min after 26 minutes.

This condensed tannin, or the tannin obtained by any of the extraction procedures, may be converted into a non-toxic salt such as an alkali metal salt, e.g., the sodium or potassium salt, which can also be used in the inactivation method of the invention.

The chemical nature of the condensed tannin was confirmed by the following tests. The material was boiled in 20% aqueous hydrochloric acid for 3 minutes. A major portion of the tannin was obtained as a phlobaphene-like precipitate which was filtered off. The reddish purple filtrate contained cyanidin and delphinidin.

The substance was also heated at 100° C. in n-butanol containing 5% hydrochloric acid for two hours. The anthocyanidins thus formed were isolated and quantitatively determined to show a ratio of cyanidin to delphinidin of 1:3.

A sample of the condensed tannin was subjected to fusion with an alkali at 185° C. under nitrogen for ten minutes to afford protocatechuic acid and gallic acid at a ratio of 1:3, in addition to some phloroglucinol.

These tests, together with the physical characteristics listed above indicate that the condensed tannin is indeed a single condensed tannin containing as a structural unit gallocatechin and catechin.

Persimmon tannin, especially the purified condensed tannin, appears to be considerably less toxic than tannic acid. Thus, the peritoneal stimulating syndrome (e.g., retention of ascites or adhesion of the peritoneum and the like) was not observed in Wistar-Imamichi strain male rats of body weight 200 to 250 g when 0.1 ml of a 0.5% aqueous solution of the tannin was injected intraperitoneally. Peritoneal irritation is observed on injection of 1-5% aqueous solutions, but no deaths are observed. Injection of 0.1 ml of a 1% aqueous solution intravenously at the tail is not lethal, but injection of 0.1 ml of a 2% aqueous solution does cause some fatalities.

No local irritation or swelling is seen when 0.05 ml of a 1.25% aqueous solution of persimmon tannin is injected into the plantar region of the paw of ddY-strain male mice (5 weeks old). In contrast, a strong irritation is observed when only a 0.1% aqueous solution of tannic acid (pharmacopoeia grade) is injected.

A model test for the inactivation of toxins and attenuation of substances producing side-effects involves observing the action of the tannin on various snake venoms.

TEST A

In a test tube, 0.1 ml of a solution of 40γ of the venom of the Erabu sea snake (*Lacticauda semifasciata*) in distilled water was neutralised with an equal amount of an aqueous solution of the tannin and the resulting solution is injected intraperitoneally into 5 week old ddY-strain male mice. The venom is found to be inactivated at a tannin concentration of at most 0.039%, while the purified condensed tannin is effective at a concentration of 0.025%. In contrast, the venom is not inactivated by tannic acid J.P. concentrations of up to 1.25%.

TEST B

In an in vitro test in which 0.1 ml of a solution of 20γ of the venom of the Habu snake (*Trimeresurus flavoviridis*) in distilled water was admixed with 0.1 ml of an aqueous solution of persimmon tannin, subcutaneous bleeding in rabbits was inhibited at a concentration of 0.078% or above. A concentration of at least 5% is required for similar inhibition by tannic acid J.P.

TEST C

Snake venom bound with persimmon tannin cannot be separated with a centrifuge and no precipitation line is observed in a precipitation reaction with antiserum using the gel-difusion method. In contrast, tannic acid J.P. bound to snake venom can be separated on a centrifuge whereupon the venom again becomes virulent. Also, a precipitation line is observed in a precipitation reaction by the gel difusion method.

Persimmon tannin, especially the condensed tannin defined above can thus be used for the inactivation of toxins, particularly microbial toxins. Particular toxins of interest are those from bacteria such as *Bordetella pertussis, Corynebacterium diphtheriae, Clostridium tetani, Clostridium botulinum,* Staphylococcus; and Streptococcus. Attenuation of substances producing side-effects e.g., pyrogens in vaccines such as typhoid, paratyphoid, cholera, pertussis, equine strangles and anthrax can also be attenuated.

While tannin from the fruit of the persimmon itself is preferred, the fruits of other species of Diospyros can equally be used.

The amount of tannin to be added to the toxin or vaccine will, of course, vary depending on the nature of the toxin or vaccine and the strength. In general it will be satisfactory to add a minor amount of an aqueous solution having a persimmon tannin concentration of not more than 0.1%.

The use of persimmon tannin, particularly the condensed tannin has a number of advantages, which may be summarised as follows:

(1) pronounced inactivation of a toxic action can be achieved using a relatively small amount of the tannin so that little consideration need be paid to any toxicity of the tannin itself;

(2) aqueous solutions of the tannin are thermally stable;

(3) an irreversible bond with toxic substances is formed;

(4) the desired antigenicity is maintained when a toxin is inactivated or a substance producing side-effects is attenuated; and (5) the material may be easily obtained by a simple method in good yield from a readily available starting material.

The following Examples illustrate the invention further.

EXAMPLE 1

EXTRACTION AND ISOLATION OF CONDENSED TANNIN

Persimmon fruits (*Diospyros Kaki* Thumb.) having seeds and calyces removed (10 kg) and a small amount of distilled water were heated to 120° C. for about 1 hour. The fruit was then minced and 15 liters of acetone were added and the mixture left to soak at ambient temperature for 24 hours. The mixture was then filtered and the filtrate concentrated under reduced pressure to about 2 liters. To this concentrate 10 liters of methanol were added and the mixture again filtered. To the filtrate were added 6–10 liters of diethyl ether and the precipitate which separated was recovered. The precipitate was dissolved in 7.5 liters of distilled water, adjusted to pH 4 with dilute hydrochloric acid, placed in a cellulose tube and then dialysed against running water. The contents of the tube were then filtered and sterilised under high pressure at 120° C. for 20 minutes. The resulting aqueous solution was freeze-dried to give 50 g of condensed tannin as a pale-brown fine powder.

Similar material can be obtained using fruits of *Diospyros lotus* and *Diospyros ebenum*.

EXAMPLE 2

INACTIVATION OF ALPHA STREPTOCOCCUS TOXIN (a) The toxin employed had a minimum lethal dose (M.L.D.) of 0.55 mcg in R.F.V.L./strain male mice having a body weight of 25 g±2 g.

To 0.1 ml samples of toxin solutions containing 1.1 mcg (2 MLD) were admixed equal volumes of aqueous persimmon tannin solutions prepared by multiple dilution of 0.5% up to 0.0019%. The mixtures were left at ambient temperature for 10 minutes and groups of 3 animals were each intraveneously injected with 0.2 ml of the mixture per animal. The state of the animals was then observed fo 48 hours. In a controlled experiment samples of the toxin were mixed with equal volumes of tannic acid solutions containing up to 0.1%.

At persimmon tannin concentrations of more than 0.0039% at least some animals survived and at a concentration of 0.0078% or higher all animals survived. In contrast, all animals died in the 24 hours following administration when tannic acid was used, even at a concentration of 0.1%.

(b) The above test used a relatively crude tannin extract which had not been dialysed. Using the purified condensed tannin, this time in ddY-strain male mice having a body weight of 25=2 g, at concentrations of 1.5, 2.0 and 2.5 MLD per 0.1 ml, the following results were obtained.

Protection against fatalities was observed at a concentration of 0.00125% when 1.5 MLD was injected and at 0.0025% when 2.5 MLD was injected.

EXAMPLE 3

INACTIVATION OF PERTUSSIS GUNDEL TOXIN

The toxin used was a supernatant prepared from 200 mcg/ml of living microorganisms by ultrasonic disintegration and subsequent refrigerated centrifugation at 10,000 g for 30 minutes. This toxic solution produce local bleeding in a guinea pig on subcutaneous injection of 0.05 ml of a 1,000-fold diluted solution.

For the test, the toxic solution was diluted 100 times and then mixed with an equal volume of an aqueous persimmon tannin solution. Different mixtures were made containing different concentrations of tannin. The mixtures were left for 10 minutes and a 0.1 ml portion was then subcutaneously injected into guinea pigs. After 24 hours inactivation was estimated by observation of induced bleeding.

Results: at an aqueous tannin concentration of 0.125%, no bleeding was observed. Slight bleeding was observed in the case of a 0.031% solution, although this bleeding was less than that produced by a 100-fold dilution of the toxin used as a control.

EXAMPLE 4

REDUCTION IN LEUCOCYTE INCREASE BY PERTUSSIS VACCINE

Reduction in leucocyte increase, considered to be a side-effect of pertussis vaccine when injected, was examined using aqueous persimmon tannin samples, including the purified condensed tannin.

Method: the pertussis vaccine used was a suspension in phosphate buffer which contained 40 billion/ml of *Bordetella pertussis* and thimerosal at a 1/10,000 concentration. Equal volumes of the pertussis suspension and persimmon tannin solutions having various concentrations were mixed and left at ambient temperature for 10 minutes. The mixtures (0.5 ml portions) were then intraperitoneally injected into ddY-strain male mice (4 weeks old) and the number of peripheral leucocytes in each animal was determined after 72 hours.

As controls, there were used two groups of animals, one of which was injected with a twice diluted sample of the pertussis suspension in phosphate buffer and the other injected only with the phosphate buffer. The results are shown in the following Table. In the Table, column A refers to the use of a relatively crude persimmon tannin extract while column B refers to the use of a purified condensed tannin.

| | Table for Example 4 | | |
|---|---|---|---|
| | Tannin Concentration | Number of leucocytes (Average of 5 animals) | |
| | % | A | B |
| Treated animals | 0.1 | 4860 | 4750 |
| | 0.02 | 6200 | 5200 |
| | 0.004 | 13320 | 11300 |
| | 0.0008 | 26620 | 24500 |
| Control | B. pertussis 22820 only | 22820 | |
| | Buffer only | 4310 | 4310 |

It can be seen from the results that a complete inhibition of leucocyte increase can be achieved at a persimmon tannin concentration of 0.1%, while a moderate effect on leucocyte increase is exerted at lower concentrations, a concentration of 0.004% being sufficient to reduce the leucocyte increase to about half its normal value.

EXAMPLE 5

INFLUENCE UPON ANTIGENICITY OF PERTUSSIS VACCINE

Using the same microorganism suspension as in Example 4 above and a 0.04% aqueous solution of persimmon tannin, equal volumes of the two liquids were mixed. As a control the twice diluted microorganisms suspension in phosphate buffer was used.

These vaccines were diluted 5, 25 and 125 times and then intraperitoneally injected into ddY-strain male mice (4 weeks old) in 0.5 ml portions.

Ten days after the injection, the animals were intracerebrally challenged with the live microorganism and thereafter the survival of the animals was observed over 14 days. No significant difference was noted in the survival of the animals. Accordingly, it was seen that the immunogenic effect in every case was the same and the persimmon tannin had no adverse effect on antigenicity.

EXAMPLE 6

INACTIVATION OF DIPHTHERIA TOXIN

Purified diphtheria toxin was diluted from 200 to 3,200 times and an equal volume of a 0.2% aqueous solution of persimmon tannin was mixed with each dilute liquid. Controlled samples were obtained by mixing physiological saline solution instead of persimmon tannin.

Hartley strain male guinea pigs having an average body weight of 300±10 g were divided into groups of three animals. Each animal was subcutaneously injected with 0.2 ml of the test liquid in the dorsal region and the survival was observed for 7 days.

Results: the controlled group of animals was observed to die within 24 hours of injection with the 200 and 400-fold dilutions of toxin, and within 48 hours in the case of injection with 800-fold dilutions of toxin. Animals treated with toxin solutions diluted at least 1600 time survived.

All animals in the group treated with toxin plus tannin survived.

Autopsy of the guinea pigs which had died indicated noticable bleeding in the adrenal glands in every case.

EXAMPLE 7

ATTENUATION OF TETANUS TOXIN

Equal volumes of tetanus toxin solution and aqueous persimmon tannin solution were mixed and left at room temperature for 10 minutes. R.F.V.L/strain female mice having an average body weight of 23±2 g were divided into groups of 3 and each animal was subcutaneously injected with 0.4 ml of the test liquid prepared as above. A series of experiments was conducted, using successive samples in which the tannin was diluted while the quantity of toxin was maintained constant;

Results: when tetanus toxin was applied at 150 MLD all the animals died within 24 hours when only the toxin was injected.

(i) All the animals survived with a tannin solution of 0.75%, but all died with a tannin solution of 0.375%.
(ii) All animals survived with a condensed tannin solution of 0.5%, but all animals died with a condensed tannin concentration of 0.25% the average time of death was 72 hours.

From these results it will be seen that tetanus toxin is effectively attenuated by persimmon tannin.

EXAMPLE 8

EVALUATION OF PERSIMMON TANNIN USING SNAKE VENOM

Method: the venom of the Erabu sea snake (*Lacticauda semifasciata*) (40γ) in 0.1 ml was mixed with an equal volume of solutions of the purified condensed tannin at various dilutions. The resulting mixture was injected intramuscularly into ddY-strain female mice (5 weeks old; 40γ of venom equals 2 MLD).

Results: protection against fatality was observed using 0.025% solutions of the condensed tannin. Protection against 4 MLD required 0.05% and against 6 MLD required 0.1% tannin solutions.

We claim:
1. A method for the inactivation of a microbial toxin or the attenuation of a vaccine, which comprises contacting the toxin or including in the vaccine, an effective amount of tannin derived from fruit of the genus Diospyros.
2. The method of claim 1 in which the tannin is derived from a specie of Diospyros selected from the group consisting of *D. Kaki, D. lotus* and *D. ebenum*.
3. The method of claim 1 in which the tannin is obtained by a process comprising the steps of
   (a) extracting the fruit with an extraction solvent selected from the group consisting of water, a water-miscible organic solvent and a mixture of two or more thereof, and removing insoluble matter;
   (b) except where an alcoholic extraction solvent is used in step (a), concentrating the liquid extract, diluting with a lower alcohol and removing insoluble matter;
   (c) precipitating tannin by adding to the alcoholic phase a non-solvent for tannin; and
   (d) dissolving the precipitated tannin in water, sterilising the solution and freeze-drying.
4. The method of claim 3 in which, in step (d), the solution is dialysed before sterilisation.
5. The method of claim 4 in which the aqueous solution is dialysed at an acid pH.
6. The method of claim 3 in which the extraction solvent of step (a) is acetone.
7. The method of claim 3 in which the non-solvent for tannin of step (c) is an aliphatic ether.
8. The method of claim 3 in which the fruit is first heated before being extracted in step (a).
9. The method of claim 8 in which the fruit is heated at 100 to 120° C.
10. The method of claim 1 in which the fruit is unripe.
11. The method of claim 1 in which the microbial toxin is derived from a strain selected from the group consisting of strains of Streptococcus, *Bordetella pertussis*, Clostridium sp and *Corynebacterium diphtheriae*.
12. A method for the inactivation of a microbial toxin or the attenuation of a vaccine, which comprises contacting the toxin or including in the vaccine an effective amount of a condensed tannin derived from fruit of the genus Diospyros, having the following properties:
   (a) a pale-brown powder in the freeze-dried state;
   (b) soluble in water; sparingly soluble in methanol, ethanol, pyridine, acidic acid; insoluble in diethyl ether, ethyl acetate, chloroform;
   (c) aqueous solution gives a dark blue coloration with ferric chloride and a brown coloration with lead acetate;
   (d) an infra-red absorption spectrum in liquid paraffin, having main absorption bands at 3400, 1615, 1530, 1380, 1200, 1100 and 1040 $cm^{-1}$;
   (e) an ultra-violet absorption spectrum measured in an aqueous solution, having an absorption maximum at about 275 nm;
   (f) a chromatogram having a single peak in a gel filtration using a strongly acidic styrene-divinylbenzene copolymer sulphonate resin and water as a mobile phase; and
   (g) an ultra-centrifuge Schlieren pattern substantially as shown in FIG. 4 herein before at about 46,633 revs/min for 26 minutes; or a salt thereof.

13. A pharmaceutical composition containing a microbial antigen treated with an effective amount of tannin derived from fruit of the genus *Diospyros*.

14. The composition of claim 13 containing tannin derived from the fruit of the genus Diospyros having the following properties:
   (a) a pale brown powder in the freeze-dried state;
   (b) soluble in water; sparingly soluble in methanol, ethanol, pyridine, acidic acid, insoluble in diethyl ether, ethyl acetate, chloroform;
   (c) aqueous solution gives a dark blue coloration with ferric chloride and a brown coloration with lead acetate;
   (d) an infrared absorption spectrum in liquid paraffin having main absorption bands at 3400, 1615, 1530, 1380, 1200, 1100 and 1040 cm$^{-1}$;
   (e) an ultraviolet absorption spectrum measured in an aqueous solution, having an absorption maximum at about 275 nm;
   (f) a chromatogram having a single peak in a gel filtration using a strongly acidic styrene-divinylbenzene copolymer sulfonate resin and water as a mobile phase; and
   (g) an ultracentrifuge Schlieren pattern substantially as shown in FIG. 4 herein before at about 46,633 revs/min for 26 minutes;
or a salt thereof.

* * * * *